(12) United States Patent
Liu et al.

(10) Patent No.: US 10,718,002 B2
(45) Date of Patent: Jul. 21, 2020

(54) QUICK SCREENING METHOD FOR MICROBIAL STRAINS AND CULTURE MEDIUM FOR THE SAME

(71) Applicant: I-SHOU UNIVERSITY, Kaohsiung (TW)

(72) Inventors: Hsiao-Han Liu, Kaohsiung (TW); Zhi-Long Tang, Kaohsiung (TW); Ting-An Kuo, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 0 days.

(21) Appl. No.: 15/847,860

(22) Filed: Dec. 19, 2017

(65) Prior Publication Data

US 2018/0208959 A1 Jul. 26, 2018

(30) Foreign Application Priority Data

Jan. 24, 2017 (TW) .............................. 106102639 A

(51) Int. Cl.
*C12Q 1/04* (2006.01)

(52) U.S. Cl.
CPC ................ *C12Q 1/04* (2013.01); *C12Q 1/045* (2013.01)

(58) Field of Classification Search
CPC .................................. C12Q 1/04; C12Q 1/045
See application file for complete search history.

(56) References Cited

U.S. PATENT DOCUMENTS

2015/0247018 A1  9/2015  Yang et al.

FOREIGN PATENT DOCUMENTS

| CN | 101717525 A | 6/2010 |
|---|---|---|
| CN | 104232501 A | 12/2014 |

OTHER PUBLICATIONS

Yoon et al., J Bioened Biodegrad., 2012, 3(4):1-8 as printed.*
Yang et al, "Biodegradation and Mineralization of Polystyrene by Plastic-Eating Mealworms: Part 2. Role of Gut Microorganisms," Environ. Sci. Technol., Oct. 20, 2015; 49 (20):12087-93.

* cited by examiner

*Primary Examiner* — Bin Shen

(57) ABSTRACT

A quick screening method for microbial strains includes the steps of: feeding a carrier worm with Styrofoam for a plurality of days; and sampling a digestive system of the carrier worm and placing the sampled digestive system of the carrier worm into a culture medium. The digestive system of the carrier worm includes at least one Styrofoam degrading microbial strain. The culture medium includes an emulsion formed by dissolving the Styrofoam with chloroform and adding a surfactant to the dissolved Styrofoam. A culture medium for fast culturing of the at least one microbial strain is also provided.

6 Claims, 2 Drawing Sheets

QUICK SCREENING METHOD FOR MICROBIAL STRAINS AND CULTURE MEDIUM FOR THE SAME

FIELD OF THE INVENTION

The present invention relates to a quick screening method for microbial strains and a culture medium for the quick screening method, and more particularly to a quick screening method for STYROFOAM (polystyrene foam) degrading microbial strains and a culture medium for the same.

BACKGROUND OF THE INVENTION

Styrofoam is a type of foam plastic made of polystyrene foam, which is an extensively used but non-degradable man-made product. As a result, recycling of STYROFOAM (polystyrene foam) has become a critical issue to countries around the world.

In Taiwan, existing commercial method for recycling STYROFOAM (polystyrene foam) involves chopping, cleaning, heat treating, and drying STYROFOAM (polystyrene foam) to obtain polystyrene particles, which can be processed to form plastic products such as toys, penholders, flower pots, camera cases, and video cassettes, or be used as synthetic construction materials.

However, heat treating of STYROFOAM (polystyrene foam) generates toxic gases such as dioxin and may irreversibly harm the environment if the toxic gases are not treated properly.

Presently, many research institutions have been focusing on biodegradation of STYROFOAM (polystyrene foam). Technically, STYROFOAM (polystyrene foam) can be degraded by internal bacteria of *Tenebrio molitor*. However, such studies are still under development. In order to screen out STYROFOAM (polystyrene foam) degrading strains, weeks of observation on loss of STYROFOAM (polystyrene foam) mass or change in STYROFOAM (polystyrene foam) structure are required after collection of the strains. Therefore, there is a need for a quick strain screening method to improve efficiency of studies in the field and development of related technologies.

Thus, the present invention provides a quick screening method for microbial strains and a culture medium for the quick screening method to solve above-mentioned problems.

SUMMARY OF THE INVENTION

An aspect of the present invention provides a quick screening method for microbial strains and a culture medium for the same, so that at least one STYROFOAM (polystyrene foam) degrading strain can be screened out expeditedly, facilitating further research on related strains in the future.

The present invention relates to a quick screening method for microbial strains and a culture medium for the same to screen out at least one STYROFOAM (polystyrene foam) degrading strain expeditedly.

The quick screening method for microbial strains includes the following steps: feeding a carrier worm with STYROFOAM (polystyrene foam) for a plurality of days; and sampling a digestive system of the carrier worm and placing the sampled digestive system of the carrier worm into a culture medium.

The carrier worm is fed with STYROFOAM (polystyrene foam) for preferably over 15 days. The digestive system of the carrier worm includes at least one STYROFOAM (polystyrene foam) degrading strain. The carrier worm may be *Tenebrio molitor* or *Zophobas*. The culture medium includes agar, an emulsion, a yeast extract solution, and a first basal medium. The emulsion is formed by dissolving the STYROFOAM (polystyrene foam) with chloroform, adding a surfactant containing a second basal medium to the dissolved STYROFOAM (polystyrene foam), and evaporating the chloroform. Herein, the surfactant is preferably a dishwasher detergent (e.g. SALATT).

Therefore, in the quick screening method for microbial strains and a culture medium for the same of the present invention, at least one STYROFOAM (polystyrene foam) degrading strain can be screened out expeditedly by utilizing the predetermined steps and the emulsion, especially by the surfactant (e.g. dishwasher detergent, for example, SALATT) in the emulsion, thus facilitating further research on related strains in the future.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
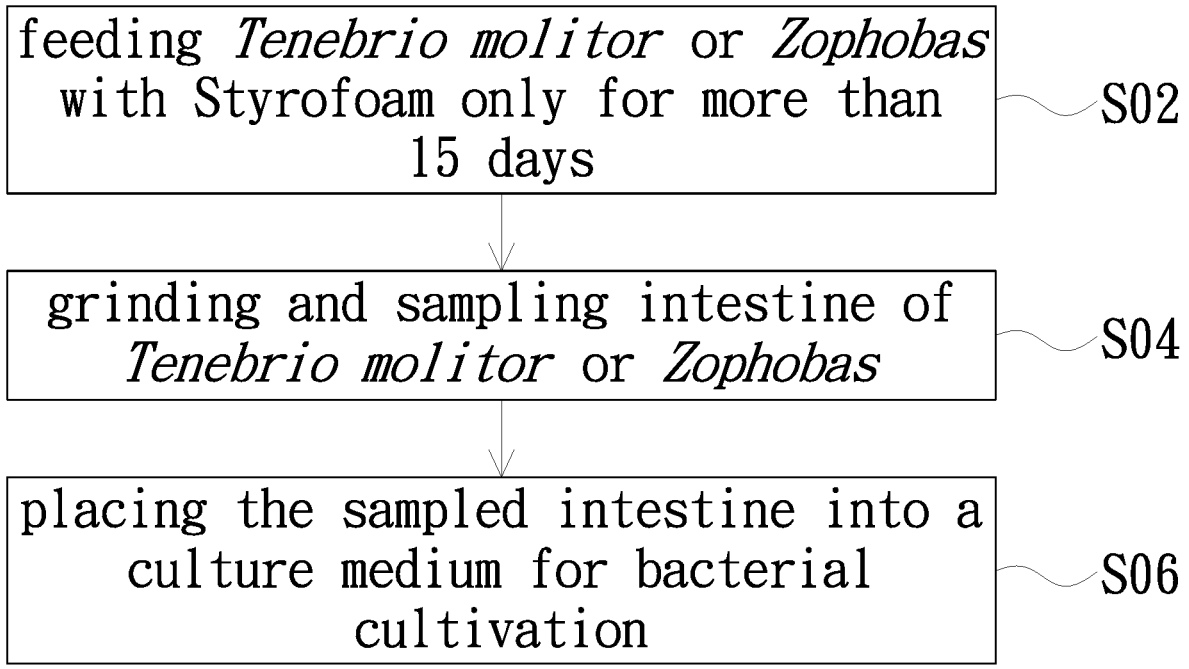
FIG. 1 is a flow chart showing a quick screening method for microbial strains according to an embodiment of the present invention.

The present invention relates to a quick screening method for microbial strains and a culture medium for the quick screening method to expeditedly screen out at least one STYROFOAM (polystyrene foam) degrading strain. Referring to FIG. 1, FIG. 1 shows a flow chart of a quick screening method for microbial strains according to an embodiment of the present invention. The strains may be, for example, *Pantoea agglomerans* (JCM1236 strain) or *Klebsiella pneumonia* (DSM 30104 strain). The quick screening method includes steps S02, S04, and S06 as follows.

In Step 1 (S02), carrier worms such as *Tenebrio molitor* (or commonly known as mealworm) or *Zophobas* (or commonly known as super mealworm) are fed with STYROFOAM (polystyrene foam) for a plurality of days (example for more than 15 days). As the digestive system of the carrier worms such as *Tenebrio molitor* or *Zophobas* includes at least one STYROFOAM (polystyrene foam) degrading strain, density of the STYROFOAM (polystyrene foam) degrading strain in the digestive system, especially in the intestinal tract, of the carrier worms would become very high if the worms are fed with STYROFOAM (polystyrene foam) only for more than 15 days.

In Step 2 (S04), the digestive system of the carrier worms is sampled. More specifically, the intestinal tract of the carrier worms is ground and sampled. To prevent contamination by other microbes, the step is preferably performed on a clean bench, and tissues of the intestinal tract are preferably cut off by a scalpel burned over an alcohol burner and sampled by tweezers or a platinum inoculation loop burned over the alcohol burner.

In Step 3 (S06), the ground intestine obtained in Step 2 is placed into a culture medium for bacterial cultivation. The culture medium may be disposed in a petri dish in advance. After placing the ground intestine in the culture medium, colonies of the STYROFOAM (polystyrene foam) degrading strain would proliferate in a few hours, and effective strains can be unambiguously determined based on consumption of the culture medium.

The culture medium includes agar, an emulsion, a yeast extract solution, and a first basal medium. The Agar is the substrate of the culture medium, and would liquify when heated, thus easily homogenizing with other culture factors. The agar becomes a stable jelly or gel-like state when cooled, and is thus suitable for cultivation of microorganisms.

The emulsion is formed by dissolving STYROFOAM (polystyrene foam) with chloroform, adding a surfactant containing a second basal medium to the dissolved STYROFOAM (polystyrene foam), and evaporating the chloroform under 4° C. for 2 days. The surfactant may be a dishwasher detergent (e.g. SALATT); however, it is to be noted that dishwasher detergents containing antiseptic agents are not preferred.

The yeast extract solution is a pure natural product in the form of a brown-yellow soluble paste or a light-yellow powder refined by degrading proteins and nucleic acids in protein-rich edible yeast cells by modern biotechnologies such as self-dissolution, enzymatic hydrolysis, isolation and concentration. Contents in the yeast extract solution are mainly polypeptides, amino acids, nucleotides, vitamin B and trace elements, allowing significant improvements in production rate of bacteria and making the yeast extract solution an ideal raw material for biological culture media and a main ingredient used in the fermentation industry.

Contents in the first basal medium and the second basal medium are identical, and may include sodium chloride (NaCl), ammonium sulfate [$(NH_4)_2SO_4$)], dipotassium hydrogen phosphate ($K_2HPO_4$), potassium dihydrogen phosphate ($KH_2PO_4$), Calcium chloride ($CaCl_2$), ferric sulfate heptahydrate ($FeSO_4.7H_2O$), and magnesium sulfate heptahydrate ($MgSO_4.7H_2O$). The first basal medium and the second basal medium provide the necessary elements for microbial proliferation.

The culture medium is formed by heating the agar into a fluid state, and mixing culture factors such as the emulsion, the yeast extract solution, and the first basal medium with the fluid agar. Meanwhile, a high temperature autoclaving is simultaneously performed, so that a desired medium is obtained and can be poured into petri dishes, test tubes or other culture flasks for subsequent cultivations.

Figure 2A:
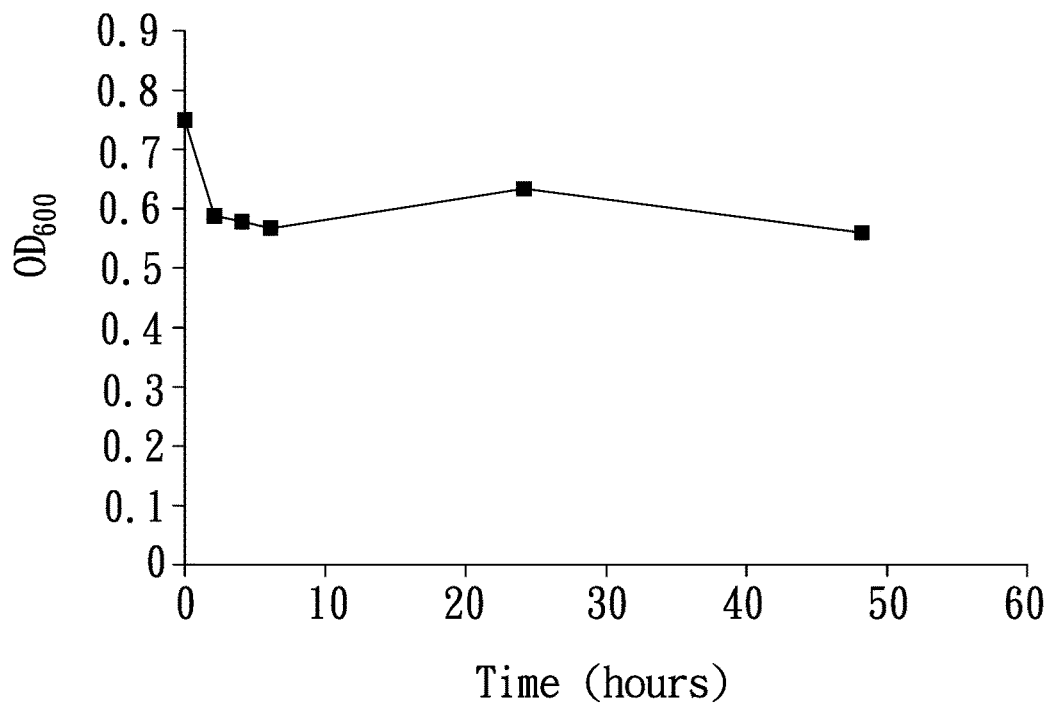
FIG. 2A is a turbidity-time diagram of an experiment using *Tenebrio molitor* as the carrier worm.
Figure 2B:
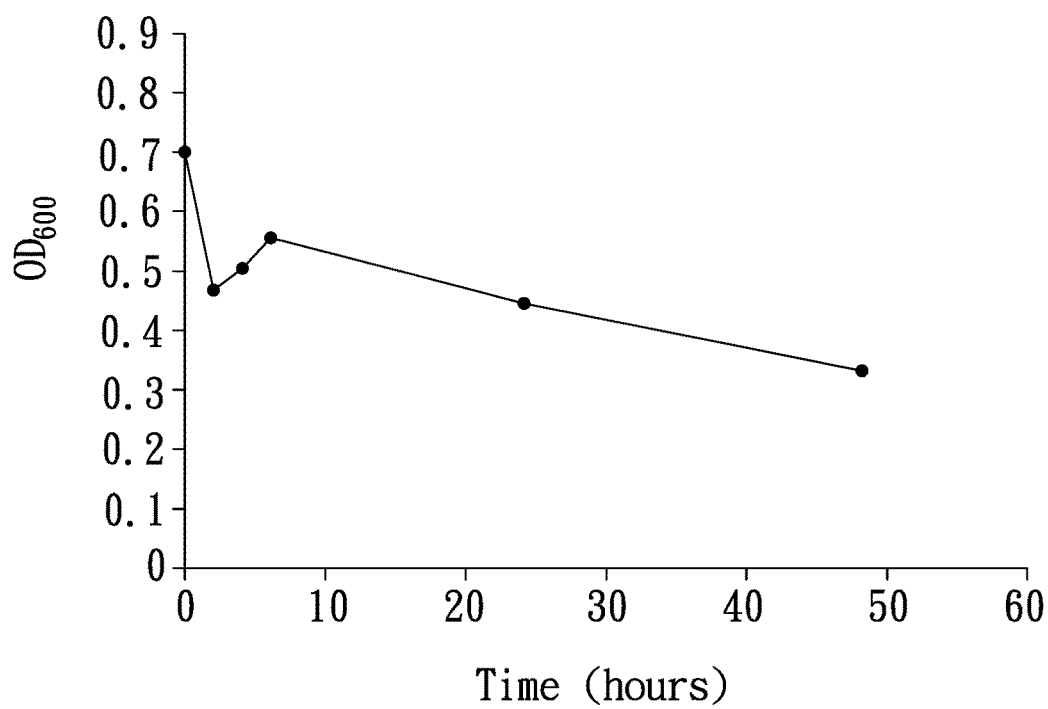
FIG. 2B is a turbidity-time diagram of an experiment using *Zophobas* as the carrier worm.

Referring to FIGS. 2A and 2B. FIG. 2A is a turbidity-time diagram of an experiment using *Tenebrio molitor* as the carrier worm, and FIG. 2B is a turbidity-time diagram of an experiment using *Zophobas* as the carrier worm. The abovementioned culture medium and quick screening method for microbial strains are used in the turbidity experiment performed at 24° C.-37° C., and optical measurement at OD600 was performed by a spectrometer. Referring to FIG. 2A, when using *Tenebrio molitor* as the carrier worm, a significant decrease in turbidity from about 0.7 to under 0.6 is observed in two hours, demonstrating that the strains had effectively degraded STYROFOAM (polystyrene foam).

In addition, referring to FIG. 2B, when using *Zophobas* as the carrier worm, a significant decrease in turbidity from about 0.7 to under 0.5 is observed in two hours, demonstrating that the strains had more effectively degraded STYROFOAM (polystyrene foam).

In sum, in the quick screening method for microbial strains and a culture medium for the same of the present invention, at least one STYROFOAM (polystyrene foam) degrading strain can be screened out expeditedly by utilizing the predetermined steps and the emulsion, especially by the surfactant (e.g. dishwasher detergent, for example, SALATT) in the emulsion, thus facilitating further research on related strains in the future.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A quick screening method for microbial strains, comprising steps of:
    (a) providing a carrier worm, wherein a digestive system of the carrier worm comprises at least one polystyrene foam degrading microbial strain, and the carrier worm is *Tenebrio molitor* or *Zophobas* and has been fed with a polystyrene foam; and
    (b) forming a culture medium within less than five days, wherein the culture medium comprises an agar, a first basal medium, a yeast extract solution and an emulsion formed by dissolving the polystyrene foam with a chloroform and adding an antiseptic agent-free surfactant to the dissolved polystyrene foam, and the first basal medium comprises a sodium chloride (NaCl), an ammonium sulfate [$(NH_4)_2SO_4$], a dipotassium hydrogen phosphate ($K_2HPO_4$), a potassium dihydrogen phosphate ($KH_2PO_4$), a Calcium chloride ($CaCl_2$), a ferric sulfate heptahydrate ($FeSO_4.7H_2O$), and a magnesium sulfate heptahydrate ($MgSO_4.7H_2O$);
    (c) sampling the digestive system of the carrier worm and placing the sampled digestive system of the carrier worm into the culture medium to enable the at least one polystyrene foam degrading microbial strain to proliferate for a few hours; and
    (d) determining and selecting at least one effective strain based on consumption of the culture medium within a few hours.

2. The quick screening method for microbial strains according to claim 1, wherein the step of (b) comprises steps of:
    (b-1) forming the emulsion, comprising:
    dissolving the polystyrene foam with the chloroform; and adding the surfactant to the dissolved polystyrene foam;
    (b-2) heating the agar into a fluid state, and mixing the agar, the first basal medium, the yeast extract solution and the emulsion; and
    (b-3) cooling the mixture from the step of (b-2).

3. The quick screening method for microbial strains according to claim 2, wherein the step of (b-1) further comprises steps of:
    (b-1-1) forming a second basal medium, wherein the second basal medium comprises a sodium chloride (NaCl), an ammonium sulfate [$(NH_4)_2SO_4$], a dipotassium hydrogen phosphate ($K_2HPO_4$), a potassium dihydrogen phosphate (KH$_2$PO$_4$), a Calcium chloride (CaCl$_2$), a ferric sulfate heptahydrate (FeSO$_4$.7H$_2$O), and a magnesium sulfate heptahydrate (MgSO$_4$.7H$_2$O);

(b-1-2) adding the second basal medium together with the surfactant to the dissolved polystyrene foam; and (b-1-3) evaporating the chloroform.

4. The quick screening method for microbial strains according to claim 1, wherein the surfactant is a dishwasher detergent.

5. The quick screening method for microbial strains according to claim 1, wherein the step of providing a carrier worm comprises feeding the carrier worm with the polystyrene foam for more than 15 days.

6. The quick screening method for microbial strains according to claim 1, wherein the step of sampling the digestive system of the carrier worm comprises grinding and sampling an intestine of the carrier worm.

\* \* \* \* \*